United States Patent [19]

Linsky et al.

[11] 4,181,127

[45] Jan. 1, 1980

[54] BALANCED ENVIRONMENT WOUND DRESSING

[75] Inventors: Cary B. Linsky, East Brunswick; David T. Rovee, Somerset, both of N.J.

[73] Assignee: Johnson & Johnson, New Brunswick, N.J.

[21] Appl. No.: 920,530

[22] Filed: Jun. 29, 1978

[51] Int. Cl.² ............................................. A61F 13/00
[52] U.S. Cl. ..................................... 128/155; 128/149
[58] Field of Search ............................... 128/153–157, 128/149

[56] References Cited

U.S. PATENT DOCUMENTS

| | | | |
|---|---|---|---|
| 2,273,873 | 2/1942 | Klein | 128/156 |
| 2,577,945 | 12/1951 | Atherton | 128/156 |
| 3,285,245 | 11/1966 | Eldredge et al. | 128/156 |
| 3,508,544 | 4/1970 | Moore et al. | 128/149 |
| 3,521,631 | 7/1970 | Gardner et al. | 128/156 |
| 3,972,328 | 8/1976 | Chen | 128/156 |

Primary Examiner—Lawrence W. Trapp
Attorney, Agent, or Firm—Irving Newman

[57] ABSTRACT

A non-occlusive, non-adherent dressing for wounds, the dressing comprising an imperforate (i.e. continuous) flexible film for contacting the wound, and an absorbent pad backing the wound-contacting film and extending beyond a substantial portion of the periphery of the film, the dressing having vapor transport cavity approximating that of intact human skin. The absorbent pad removes wound exudate from the proximate area of the wound without the pad coming into contact with the open wound itself. The final construction, comprising the film and absorbent backing, permits a measurable amount of moisture vapor to be transmitted (greater than 0.06 mg/cm²/hr), thereby greatly reducing the degree of maceration and other problems that may be produced by a fully occlusive dressing.

6 Claims, 6 Drawing Figures

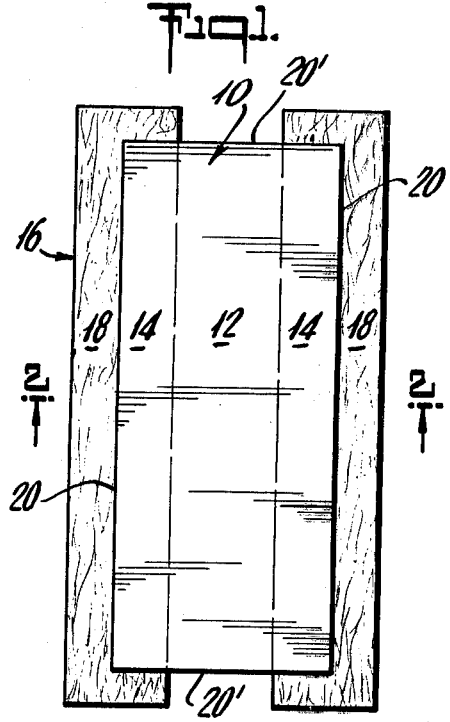
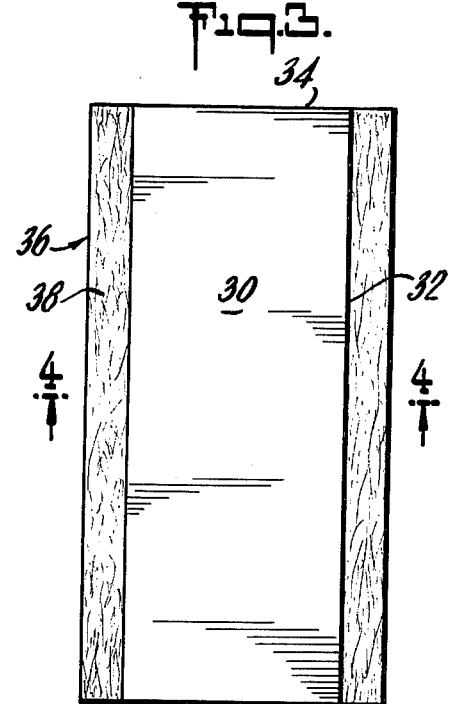
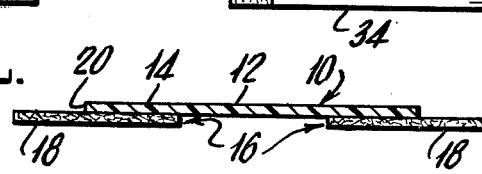
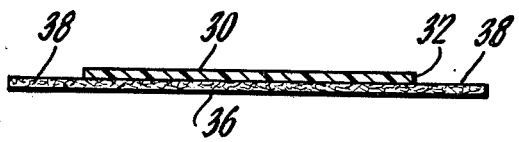
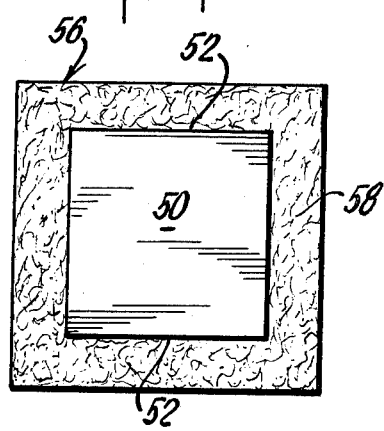
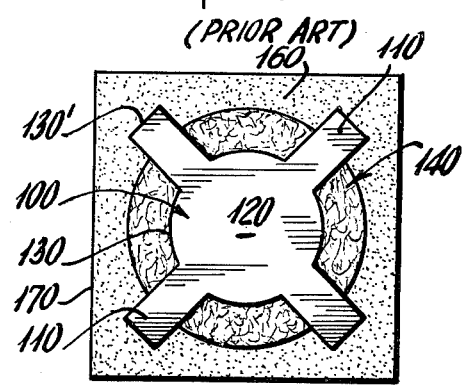

BALANCED ENVIRONMENT WOUND DRESSING

TECHNICAL FIELD

This invention relates to wound dressings. More particularly, it relates to dressings that can be used in contact with exuding wounds and have the capacity to absorb wound exudate while remaining essentially non-adherent to the wound and providing a desirable level of vapor transport.

BACKGROUND ART

It has been shown that there is a tendency for wounds to heal more rapidly if the escape of moisture from the wound is controlled, i.e. the desiccation associated with air-exposed wounds is avoided. The above benefits associated with occlusive therapy however are often accompanied by recognized disadvantages in the clinic. These problems include the promotion of a wet wound surface, a surface which is prone to problems of secondary infection. Such a wet surface is also difficult to seal to a dressing. The problems of the skin being continuously hydrated and softened (i.e. maceration) also are seen with occlusive therapy.

It has been previously proposed to utilize dressings comprising a smooth flexible film in contact with a wound surface. Thus, metal sheeting and organic polymeric films have been utilized for purposes of optimizing wound release (i.e. non-adherence). One expedient for handling wound exudate with this type of construction is described in U.S. Pat. No. 3,285,245, issued Nov. 15, 1966, wherein the wound-facing material is discontinuous, having been perforated or cut to allow wound exudate to pass through to a backing absorbent. As a result of such perforated construction, the wound exudate tends to dry in the channels between the wound surface and the fibrous backing absorbent, resulting in undesired adherence of the dressing to the wound at the affected perforations. If the above perforations are made too small, then wound exudate soon plugs the openings, resulting in an inability of the exudate to reach the absorbent. This causes puddling to occur beneath the film, forming pockets of wound exudate which tend to push the film away from the surface of the wound and skin. Such pockets of wound exudate provide an excellent environment for bacterial proliferation and are thus contraindicated.

U.S. Pat. No. 3,521,631 issued on July 28, 1970 discloses a three-piece occlusive construction composed of (1) a non-adherent film-wound-facing material, (2) an absorbent pad backing the wound-facing material and (3) a flexible imperforate film backing extending beyond the edges of the aforementioned two components. Such a construction, while providing for the uptake of exudate and non-adherence, is by definition very occlusive in nature, i.e. has a moisture vapor transmission rate (MVT) that is so low as not to be measurable by the herein described techniques. Another multilayer occlusive bandage construction is described in U.S. Pat. No. 3,972,328, issued Aug. 3, 1976.

DISCLOSURE OF INVENTION

The present invention provides a non-occlusive dressing construction which is non-adherent to the wound surface, adequately absorbs wound exudates and affords sufficient vapor transfer to prevent or minimize maceration. The dressing of the invention comprises a two-layer construction wherein the first layer is a continuous, imperforate facing film for contacting the wound, such film having an adherence of less than 20 gm/cm$^2$ of wound surface and an MVT of at least about 0.08 mg/cm$^2$/hour; and the second layer is an absorbent backing which extends laterally beyond the edge of the facing film such that accumulated fluid, as it moves along the surface of the film, will be taken up or wicked by the absorbent layer. While additional layers of adhesive or backed adhesive may be included in the construction or juxtaposed with all or part of the basic two-piece construction, it is necessary that the completed dressing of the present invention have a moisture vapor transmission rate (MVT) of at least about 0.06 mg/cm$^2$/hr. As a consequence, the dressing of the present invention retains many of the advantages of simple film dressings, (i.e. good wound release, promotion of epithelization) while maintaining the ability to remove wound exudate from the surface of the wound by virtue of the absorbent component which backs the film. Moreover, by providing a dressing combining these properties with an MVT as defined herein (at least about 0.06 mg/cm$^2$/hr) we have been able to greatly diminish the previously discussed problems (such as maceration) heretofore associated with occlusive dressing therapy. While it is required, for maximum benefit, that the MVT not be too high, to avoid the desiccation effects of open air exposure mentioned above, as a practical matter such high MVT rates cannot be achieved with proper use of the wound dressing construction of the present invention.

BRIEF DESCRIPTION OF THE DRAWINGS

The invention is more readily described by reference to the drawings which show certain embodiments of the same. The embodiments illustrated in the drawings, however, are for purpose of illustration only, and the invention is not limited solely to the specific embodiments shown.

Referring to the drawings:

FIG. 1 is a plan view of a dressing made in accordance with the present invention;

FIG. 2 is a cross-sectional view of the dressing of FIG. 1 taken along line 2—2;

FIG. 3 is a plan view of another embodiment of a dressing in accordance with the present invention;

FIG. 4 is a cross-sectional view taken along line 4—4 of FIG. 3.

FIG. 5 is a plan view of yet another embodiment of a dressing in accordance with the present invention; and FIG. 6 is a plan view of an occlusive dressing made in accordance with the invention described and claimed in U.S. Pat. No. 3,521,631 and is included to illustrate the prior art and facilitate understanding of the distinctions between such occlusive dressing and dressings in accordance with the present invention as illustrated in FIGS. 1–5.

BEST MODE FOR CARRYING OUT THE INVENTION

Referring to FIGS. 1 and 2, the semi-occlusive dressing of the present invention there illustrated comprises a facing layer 10 of continuous, imperforate film for contacting the exposed surface of a wound. Facing film 10 has an MVT (moisture vapor transmission rate) of at least about 0.08 mg/cm$^2$/hr when measured on an electrolytic water analyzer at ambient temperature (22° C.) over a relative humidity gradient of 100% to 0%.

(Whenever an MVT value is given herein, it is based on this method of measurement). Such film will, by virtue of its imperforate nature, not allow a greater moisture vapor transmission rate than about 10 mg/cm$^2$/hr. Films such as the above will preferably have a smooth morphology as opposed to those that may be embossed or wrinkled, thus assuring better conformability to the wound bed.

Moreover, in accordance with the present invention, film 10 will, when in contact with a wound bed for a period of 24 hours, require no more than 20 grams of force per cm$^2$ of surface area to be removed (adherence). This adherence is measured by attaching the dressing to a spring and measuring the force required to remove the dressing from a blister bed wound. For the purposes of this test, the blister bed wound is created by applying a cantharidin-impregnated disc and, after the blister is induced, removing the top with a scalpel. The test dressing is then applied to the resulting wound for the required 24 hour period, and the force of removal measured. The adherence is obtained by dividing force, in grams, by wound area, in cm$^2$.

The dimensions of the wound-facing film component will as a practical matter be dictated by the size of the wound intended for coverage plus a sufficient overlap to allow for error in placement. Because of the need for fluid movement along the surface of the film prior to contact with the (remote) absorbent backing, there is a limit (beyond which wicking is lost and puddling occurs) to the distance from any point on the film to an edge (where the contact with the absorbent would begin). In U.S. Pat. No. 3,521,631, this dimensional limitation is given as a maximum of 0.75 inches (1.9 cm). In accordance with the present invention it has been found that film 10 may be as much as three inches (3.8 cm) wide. Thus the maximum distance of a point on the film to an edge can be at least 1.5 inches (3.8 cm) or even 2 inches (5.1 cm) while retaining efficient movement of fluid along the film into the absorbent backing (wicking). This larger distance is of importance in treating wounds with large surface areas such as abrasions, donor sites and burns.

Suitable materials that may be used as film 10 in the construction of the present invention include, but are not limited to, such synthetic organic polymer films as polyethylene, polypropylene, ionomer (a family of thermoplastic materials created by chemically linking metal ions to ethylene polymers containing acid groups—available commercially under the trademark Surlyn from DuPont), polyurethane, and acrylates. Other examples could well include materials of biological origin such as collagen films. In fact, any biologically compatible continuous film or sheet that is sufficiently conformable and has the above defined MVT and adherence characteristics may be employed as film 10.

In the illustration of FIG. 1, film 10 is transparent and is divided into a window area 12 that contacts the wound and is not in contact with the overlying absorbent material, and interface areas 14 that contact the absorbent material.

An absorbent material 16, generally in the form of pads 18, overlies interface areas 14 of film 10 and overlaps edge 20 of the film. Absorbent 16 may overlap the entire edge of film 10, if desired. However, in the illustration of FIG. 1, at portion 20', the edge of film 10 is not backed by absorbent 16. In any event, sufficient absorbent 16 should extend beyond a substantial proportion of edge 20 to provide adequate wicking. For the same reason, the distance between any point on the wound contacting portion 12 of film 10 and on edge 20 should be kept to a minimum, preferably not beyond 1.5 inches (3.8 cm).

The absorbent backing 16 must wet easily and be able to hold substantial amounts of fluid so that, as wound exudate contacts it, the exudate will be taken up and moved away from the skin. Suitable materials for use as absorbent 16 include various woven and non woven materials. The suitable non-woven materials include those prepared by using binders, as well as those that are meltblown, spunlaced or spunbonded. Various foams could also serve as such a backing, including polyurethane and polyvinylalcohol, with and without wetting agents to aid their hydrophilicity. Such fibers blends as cotton and/or rayon with polyester, polypropylene, wood pulp, nylon, acrylics, etc. may also be used, as could various hydrogels.

FIGS. 3 and 4 illustrate an alternative, simpler wound dressing construction in accordance with the present invention wherein facing film 30 is backed with a continuous layer or pad of absorbent material 36. It will be noted that, as in the construction of FIGS. 1 and 2, a portion 38 of absorbent pad 36 extends beyond edges 32 which constitute a substantial portion of the edge of film 30. Again, for convenience of construction, horizontal edges 34 of film 30 are not overlapped by absorbent pad 36.

In the wound dressing of FIG. 5, which is particularly adapted for use in an adhesive bandage construction for small wounds, all edges 52 of film 50 are overlapped by absorbent pad 56. The overlapping portion 58 that extends beyond edge 52 is of sufficient size and shape to provide adequate wicking and absorption of wound exudate.

While the wound dressing of the present invention has been illustrated as a two-element construction, it is within the scope of the present invention to have other elements present in the final construction so long as the final construction has an MVT of at least about 0.06/mg/cm$^2$/hr (measured as described above). As pointed out hereinbefore, this minimum MVT requirement ensures the non-occlusivity of the dressing, thereby avoiding such problems associated with occlusivity as maceration and bacterial proliferation.

Thus, for example, suitable adhesive may be provided on all or part of the periphery of the dressing, for securing it to the user. Alternatively, an adhesive tape having appropriate MVT characteristics may back all or part of the basic two-piece construction. Yet another alternative is for the user to secure the dressing in place by applying strips of adhesive tape or be means of an elastic bandage or other suitable securing means.

It also will be understood that the wound dressings of the present invention may be constructed by any suitable means known to the art. For example, the film and the absorbent may be joined at all or selected portions of their interface by such means at heat-sealing, adhesives, ultrasonics, sewing, radio frequency and fusible plastics. It is also within the scope of the invention to create the dressing in situ by first placing the film in contact with the wound and then suitably fixing an absorbent in contact with, and overlying a substantial portion of the edge of, the film.

Also, if desired, protective cover facings (not shown) may be provided on the dressings in manners known to the art, for removal immediately before use.

Referring to FIG. 6, the occlusive dressing there illustrated is representative of prior art occlusive dressings as disclosed and claimed in U.S. Pat. No. 3,521,631. It has a flexible sheet 100 adapted to contact the wound surface when the dressing is in place. The flexible sheet or film 100 is the wound-contacting portion of the dressing. The wound-contacting sheet 100 is so formed that no part thereof is more than 0.75 inch (1.9 cm) distance from an edge 130 of the sheet 100. In the occlusive dressing illustrated in FIG. 6, the wound-contacting flexible sheet 100 has somewhat the shape of a cross with arms 110 and center circular imperforate wound cover portion 120. The area of sheet 100 of furthest distance from an edge 130 is the area situated in the exact center of the circular wound cover portion 120. Thus, in accordance with the teaching of the U.S. Pat. No. 3,521,631, the dimensions of the wound-contacting sheet 100 are such that the diameter of the circular portion 120 is not greater than 1.5 inches (3.8 cm).

An absorbent 140 in the form of a pad backs sheet 100 and extends beyond the edge 130 of the same. As in the construction of the present invention, the absorbent pad 140 may extend beyond the entire edge 130 of the wound-contacting sheet 100 or only beyond a portion thereof as occurs in the specific embodiment illustrated wherein it extends beyond most of the edge portion with a part of the edge, such as illustrated at 130', not being backed by the absorbent.

In the illustrated occlusive dressing, the wound-contacting flexible sheet 100 and the absorbent 140 are backed by an imperforate flexible sheet 160 which is sufficiently large to extend beyond the peripheral edges of both the wound-contacting flexible sheet 100 and the backing absorbent 140.

As discussed in the U.S. Pat. No. 3,521,631, the flexible backing sheet 160 may be formed of any flexible organic film-forming material and is adapted to be secured around its edges 170 to the skin of a patient after the dressing is placed over a wound. This securing of the edges 170 may be done by taping along the edges 170 of the backing film 160 but in the construction of FIG. 6 is done by means of a pressure-sensitive adhesive which is coated over the entire surface of film 160 in the particular embodiment illustrated in FIG. 6, although it may be placed only around the peripheral edge 170 of the backing film to form an adhesive border for sealing the same to the skin of the patient. Backing film 160 is relatively impervious to moisture and forms an occlusive environment under the same.

EXAMPLE

A two-piece wound dressing in accordance with the present invention was constructed by heat sealing ionomer film to a rayon absorbent backing. When the resultant construction was measured for moisture vapor transmission rate, an MVT value of 0.4 mg/cm$^2$/hr was recorded—a rate within the normal range of that of intact human skin (between 0.1 and 1.0 mg/cm$^2$/hr). A comparative prior art construction such as that illustrated in FIG. 6 was prepared by affixing to the above two-piece construction a third piece—a flexible imperforate film backing (vinyl adhesive tape). This dressing, which is an example of that described in U.S. Pat. No. 3,521,631, gave no measurable MVT. I.e. it was occlusive.

The above two constructions were worn as adhesive bandages on the fingers of four volunteers for a period of approximately 18 hours. The two-piece construction was held in place by tape which had a window cut in it so as to prevent occlusivity. In all cases, the three-piece construction provoked greater maceration of the fingers, characterized by a greater softening and whitening of the skin, than did the two-piece construction, which is non-occlusive.

Certain specific embodiments have been utilized in illustrating the present invention. The invention, however, is not limited to these specific embodiments and may be practiced in the form of other embodiments which would be apparent to one skilled in the art having the advantage of the teaching of the present specification. The invention accordingly, is not to be limited except by the appended claims.

What is claimed is:

1. A wound dressing comprising an imperforate flexible sheet having a wound cover portion adapted to be placed in contact with and cover a wound, and an absorbent for wound exudate, said absorbent overlying at least a portion of said imperforate flexible sheet and extending beyond at least a portion of the edge of said flexible sheet, wherein said flexible sheet has an adherence of less than about 20 gm/cm$^2$ and an MVT of at least about 0.08 mg/cm$^2$hr, the distance between any point on said wound cover portion of said flexible sheet and an edge of said flexible sheet beyond which said absorbent extends is sufficiently short to prevent accumulation of wound exudate under said wound cover portion, and the MVT of said dressing is at least about 0.06 mg/cm$^2$/hr.

2. The wound dressing of claim 1 wherein said imperforate flexible sheet is a biologically compatible organic polymer film.

3. The wound dressing of claim 2 wherein said organic polymer is selected from the group consisting of polyethylene, polypropylene, ionomer, polyurethane, the acrylate polymers and collagen.

4. The wound dressing of claim 1 wherein said absorbent is selected from the group consisting of the woven and non-woven fabrics, polymerics foams, fiber blends and hydrogels.

5. The wound dressing of claim 1 wherein said distance is not more than about 5 cm.

6. The wound dressing of claim 5 wherein said distance is not more than 3.8 cm.

* * * * *